US011361436B2

(12) United States Patent
Cunningham (10) Patent No.: US 11,361,436 B2
(45) Date of Patent: Jun. 14, 2022

(54) SYSTEMS AND METHODS FOR METABOLITE TOPOGRAPHY OF THE BRAIN WITH MAGNETIC RESONANCE IMAGING

(71) Applicant: Sunnybrook Research Institute, Toronto (CA)

(72) Inventor: Charles Cunningham, Toronto (CA)

(73) Assignee: Sunnybrook Research Institute, Toronto (CA)

( * ) Notice: Subject to any disclaimer, the term of this patent is extended or adjusted under 35 U.S.C. 154(b) by 207 days.

(21) Appl. No.: 16/871,699

(22) Filed: May 11, 2020

(65) Prior Publication Data

US 2020/0357115 A1    Nov. 12, 2020

Related U.S. Application Data

(60) Provisional application No. 62/846,239, filed on May 10, 2019.

(51) Int. Cl.
| | |
|---|---|
| G06K 9/00 | (2022.01) |
| G06T 7/00 | (2017.01) |
| G01R 33/56 | (2006.01) |
| G01R 33/48 | (2006.01) |
| G06T 7/11 | (2017.01) |

(Continued)

(52) U.S. Cl.
CPC .......... *G06T 7/0012* (2013.01); *A61B 5/0042* (2013.01); *A61B 5/0044* (2013.01); *A61B 5/055* (2013.01); *A61B 5/14546* (2013.01); *G01R 33/4828* (2013.01); *G01R 33/5601* (2013.01); *G01R 33/5608* (2013.01); *G06T 7/11* (2017.01); *G06T 2200/04* (2013.01);

(Continued)

(58) Field of Classification Search
CPC ..... A61B 5/4064; A61B 5/165; A61B 5/7267; A61B 6/501; A61B 2576/026; A61B 5/0042; A61B 5/374; G06T 2207/30016; G06T 2207/10088; G06T 7/0012; G06T 2207/10104; G06T 7/0016; G06T 11/206; G06T 2207/10076; G06T 2207/20076; G06T 2207/20081; G06T 3/0093
See application file for complete search history.

(56) References Cited

U.S. PATENT DOCUMENTS

| | | | |
|---|---|---|---|
| 2013/0102877 A1* | 4/2013 | Mori .................. | G01R 33/5608 600/410 |
| 2014/0119627 A1* | 5/2014 | Skretting .............. | G06T 7/0016 382/131 |
| 2016/0341712 A1* | 11/2016 | Agar ................ | G01N 33/57496 |

OTHER PUBLICATIONS

Ardenkjaer-Larsen, J. H., et al. "Increase in signal-to-noise ratio of> 10,000 times in liquid-state NMR." Proceedings of the National Academy of Sciences of the United States of America 100.18 (2003): 10158.

(Continued)

*Primary Examiner* — Alex Kok S Liew
(74) *Attorney, Agent, or Firm* — Quarles & Brady LLP (57) ABSTRACT

Metabolite profiles are generated from magnetic resonance images. These metabolite profiles indicate a topography of the metabolites in one or more anatomical regions. The magnetic resonance images can be metabolite images, such as those obtained using hyperpolarized $^{13}$C-MRI. The metabolite profiles can be generated by parcellating the magnetic resonance images into different regions, computing z-scores for those regions, and generating the metabolite profile based on the computed z-scores.

19 Claims, 7 Drawing Sheets

(51) Int. Cl.
A61B 5/055 (2006.01)
A61B 5/00 (2006.01)
A61B 5/145 (2006.01)

(52) U.S. Cl.
CPC .............. G06T 2207/10088 (2013.01); G06T 2207/30016 (2013.01); G06T 2207/30048 (2013.01)

(56) References Cited

OTHER PUBLICATIONS

Belanger, M. et al. "Brain energy metabolism: focus on astrocyte-neuron metabolic cooperation." Cell metabolism 14.6 (2011): 724-738.
Blazey, T, et al. "Quantitative positron emission tomography reveals regional differences in aerobic glycolysis within the human brain." Journal of Cerebral Blood Flow & Metabolism 39.10 (2019): 2096-2102.
Cunningham, C. H., et al. "Hyperpolarized 13C metabolic MRI of the human heart: initial experience." Circulation research 119.11 (2016): 1177-1182.
Cunningham, C. H., et al. "Pulse sequence for dynamic volumetric imaging of hyperpolarized metabolic products." Journal of magnetic resonance 193.1 (2008): 139-146.
Day, S. E., et al. "Detecting tumor response to treatment using hyperpolarized 13 C magnetic resonance imaging and spectroscopy." Nature medicine 13.11 (2007): 1382-1387.
Diaz-García, C. M., et al. "Neuronal stimulation triggers neuronal glycolysis and not lactate uptake." Cell metabolism 26.2 (2017): 361-374.
Dienel, G. A. "Lack of appropriate stoichiometry: Strong evidence against an energetically important astrocyte-neuron lactate shuttle in brain." Journal of Neuroscience Research 95.11 (2017): 2103-2125.
Dinuzzo, M., et al. "Brain energetics during the sleep-wake cycle." Current opinion in neurobiology 47 (2017): 65-72.
Geraghty, B. J., et al. "Dual-echo EPI sequence for integrated distortion correction in 3D time-resolved hyperpolarized 13C MRI." Magnetic Resonance in Medicine 79.2 (2018): 643-653.
Gordon, J. W., et al. "Translation of Carbon-13 EPI for hyperpolarized MR molecular imaging of prostate and brain cancer patients." Magnetic resonance in medicine 81.4 (2019): 2702-2709.
Goyal, M. S., et al. "Aerobic glycolysis in the human brain is associated with development and neotenous gene expression." Cell metabolism 19.1 (2014): 49-57.
Goyal, M. S., et al. "Loss of brain aerobic glycolysis in normal human aging." Cell metabolism 26.2 (2017): 353-360.
Grist, J. T., et al. "Quantifying normal human brain metabolism using hyperpolarized [1-13C] pyruvate and magnetic resonance imaging." NeuroImage 189 (2019): 171-179.
Hyder, F., et al. "Uniform distributions of glucose oxidation and oxygen extraction in gray matter of normal human brain: no evidence of regional differences of aerobic glycolysis." Journal of Cerebral Blood Flow & Metabolism 36.5 (2016): 903-916.
Koush, Y., et al. "Functional MRS with J-edited lactate in human motor cortex at 4 T." Neuroimage 184 (2019): 101-108.
Laughton, J. D., et al. "Metabolic compartmentalization in the human cortex and hippocampus: evidence for a cell-and region-specific localization of lactate dehydrogenase 5 and pyruvate dehydrogenase." BMC neuroscience 8.1 (2007): 35.
Liang, X., et al. "Coupling of functional connectivity and regional cerebral blood flow reveals a physiological basis for network hubs of the human brain." Proceedings of the National Academy of Sciences of the United States of America 110.5 (2013): 1929.
Magistretti, P. J., et al. "Lactate in the brain: from metabolic end-product to signalling molecule." Nature Reviews Neuroscience 19.4 (2018): 235-249.
Mangia, S., et al. "Sensitivity of single-voxel 1H-MRS in investigating the metabolism of the activated human visual cortex at 7 T." Magnetic resonance imaging 24.4 (2006): 343-348.
Mecocci, P., et al. "Oxidative damage to mitochondrial DNA shows marked age-dependent increases in human brain." Annals of Neurology 34.4 (1993): 609-616.
Merboldt, K.-D., et al. "Decrease of glucose in the human visual cortex during photic stimulation." Magnetic resonance in medicine 25.1 (1992): 187-194.
Miloushev, V. Z., et al. "Metabolic imaging of the human brain with hyperpolarized 13C pyruvate demonstrates 13C lactate production in brain tumor patients." Cancer research 78.14 (2018): 3755-3760.
Nelson, S. J., et al. "Metabolic imaging of patients with prostate cancer using hyperpolarized [1 -13C] pyruvate." Science translational medicine 5.198 (2013): 198ra108-198ra108.
Pellerin, L., et al. "Evidence supporting the existence of an activity-dependent astrocyte-neuron lactate shuttle." Developmental neuroscience 20.4-5 (1998): 291-299.
Pellerin, L., et al. (1994). Glutamate uptake into astrocytes stimulates aerobic glycolysis: a mechanism coupling neuronal activity to glucose utilization. Proceedings of the National Academy of Sciences, 91(22), 10625-10629.
Prichard, J, et al. "Lactate rise detected by 1H NMR in human visual cortex during physiologic stimulation." Proceedings of the national academy of sciences 88.13 (1991): 5829-5831.
Rex, D. E., et al. "The LONI pipeline processing environment." Neuroimage 19.3 (2003): 1033-1048.
Shan, Z. Y., et al. "Cerebral glucose metabolism on positron emission tomography of children." Human brain mapping 35.5 (2014): 2297-2309.
Shattuck, D. W., et al. "Construction of a 3D probabilistic atlas of human cortical structures." Neuroimage 39.3 (2008): 1064-1080.
Subhash, M. N., et al. "Regional distribution of lactate dehydrogenase isoenzymes in human brain." Current Science (1986): 770-772.
Suzuki, A., et al. "Astrocyte neuron lactate transport is required for long term memory formation." Cell 144.5 (2011): 810-823.
Vaishnavi, S. N., et al. "Regional aerobic glycolysis in the human brain." Proceedings of the National Academy of Sciences 107.41 (2010): 17757-17762.

\* cited by examiner

SYSTEMS AND METHODS FOR METABOLITE TOPOGRAPHY OF THE BRAIN WITH MAGNETIC RESONANCE IMAGING

CROSS-REFERENCE TO RELATED APPLICATIONS

This application claims the benefit of U.S. Provisional Patent Application Ser. No. 62/846,239, filed on May 10, 2019, and entitled "SYSTEMS AND METHODS FOR METABOLITE TOPOGRAPHY OF THE BRAIN WITH MAGNETIC RESONANCE IMAGING," which is herein incorporated by reference in its entirety.

BACKGROUND

Lactate, once considered a waste product, is now recognized as an important intermediate in brain metabolism. The astrocyte-neuron lactate shuttle (ANLS) model indicates that the ATP needed to clear glutamate from synapses is primarily derived from lactate produced by aerobic glycolysis in astrocytes. There is evidence of multiple roles for lactate: a source of energy in glutamatergic neurons, a signaling molecule modulating neuronal excitability and synaptic plasticity, and a key player in maintaining homeostasis. Furthermore, experiments in rats have shown that lactate transport is required for long-term memory formation, and that cerebral aerobic glycolysis and lactate concentration are reduced during sleep.

While there continues to be debate surrounding the degree to which neurons are fueled by astrocytic lactate, mounting evidence points to a critical role of aerobic glycolysis and lactate in brain energy metabolism. Combined PET measurements of cerebral metabolic rate of oxygen and glucose using $^{15}$O-oxygen and $^{19}$F-fluorodeoxyglucose, respectively, can provide an estimate of aerobic glycolysis through a measure of the oxygen to glucose index ("OGI"), which is 6.0 if glucose is fully oxidized. These PET experiments have shown evidence of non-oxidative consumption of glucose (OGI<6.0), with net brain glucose uptake exceeding the rate required to match the regional oxygen consumption. OGI is lowest in children and young adults and increases with aging, and recently, it was shown that the OGI has a distinct topography within the brain, corresponding to regions with persistent gene expression associated with childhood development (neoteny). However, these radiotracer methods that measure OGI only allow for the calculation of the non-oxidative component of glucose consumption, and cannot measure the production of lactate that ends up being used in oxidative phosphorylation in other cell compartments. Furthermore, conventional metabolite measurement methods using MR spectroscopy only enable the measurement of the steady-state metabolite concentrations, and not the rate of metabolite production and transport.

SUMMARY OF THE DISCLOSURE

The present disclosure addresses the aforementioned drawbacks by providing a method for producing a metabolite profile from magnetic resonance images. The method includes accessing magnetic resonance images acquired from a subject. The magnetic resonance images includes, a plurality of metabolite images having pixel values indicative of magnetic resonance signals associated with a metabolite and a plurality of anatomical images that depict anatomical structures in the subject. Parcellated image data are generated by parcellating the anatomical images into a plurality of regions, wherein each pixel in the parcellated image data is associated with a region from an anatomical atlas. A metabolite profile is then generated for the subject from the plurality of metabolite images and using the parcellated image data. The metabolite profile can be generated by (i) selecting a given region from the plurality of regions; (ii) retrieving pixels values from the plurality of metabolite images using the coordinates for the given region in the parcellated image data; (iii) computing a mean pixel value for the given region by computing a mean of the retrieved pixel values; and (iv) repeating steps (i) though (iii) for each of a number of the plurality of regions in order to generate a sequence of mean pixel values, wherein the metabolite profile comprises the sequence of mean pixel values.

It is another aspect of the present disclosure to provide a method for producing a metabolite profile from magnetic resonance images. The method includes accessing magnetic resonance images acquired from a subject, where the magnetic resonance images include a plurality of metabolite images, each having pixel values indicative of magnetic resonance signals associated with a metabolite, and a plurality of anatomical images that depict anatomical structures in the subject. Parcellated image data are generated by parcellating the anatomical images into a plurality of parcellated regions, where each pixel in the parcellated image data is associated with a region from an anatomical atlas. A metabolite profile is generated for the subject from the plurality of metabolite images and using the parcellated image data. This metabolite profile is generated by (i) selecting a first region from the plurality of parcellated regions; (ii) retrieving first pixel values from the plurality of metabolite images using the coordinates for the first region in the parcellated image data; (iii) selecting a second region from the plurality of parcellated regions; (iv) retrieving second pixel values from the plurality of metabolite images using the coordinates for the second region in the parcellated image data; (v) computing a ratio value between the first pixel values and the second pixel values; and (vi) repeating steps (i) though (v) for each of a number of first and second regions in the plurality of parcellated regions in order to generate a sequence of ratio values, wherein the metabolite profile comprises the sequence of ratio values.

The foregoing and other aspects and advantages of the present disclosure will appear from the following description. In the description, reference is made to the accompanying drawings that form a part hereof, and in which there is shown by way of illustration a preferred embodiment. This embodiment does not necessarily represent the full scope of the invention, however, and reference is therefore made to the claims and herein for interpreting the scope of the invention.

DETAILED DESCRIPTION

Described here are systems and methods for generating metabolite profiles from magnetic resonance images. These metabolite profiles indicate a topography of the metabolites in one or more anatomical regions. The magnetic resonance images can be metabolite images, such as those obtained using hyperpolarized $^{13}$C-MRI. Hyperpolarized $^{13}$C-MRI is an imaging method that enables time-resolved volumetric imaging of metabolite production within tissue.

As one non-limiting example, the distribution of lactate and bicarbonate produced from intravenously injected $^{13}$C-pyruvate over the whole brain can be mapped using the methods described in the present disclosure. The metabolite images (e.g., $^{13}$C-lactate images) from each subject are parcellated into spatial regions (e.g., brain atlas regions, heart atlas regions) based on structural anatomical images in order to generate or otherwise determine the metabolite signal (e.g., lactate) from each specific brain region, such as the regions contained in the atlas. In this way, the systems and methods described here are capable of providing a "metabolite topography" in the human brain, heart, or other organ or organ system.

In some implementations, the methods described in the present disclosure can be used to generate a metabolite topography of non-hyperpolarized (e.g., endogenous) metabolites, which may include lactate, glutamate, and others.

The metabolite topographies can be generated for a particular organ or organ system, a subset of a particular organ or organ system, and/or a combination of regions from more than one organ or organ system. For instance, one or more metabolite topographies can be generated for the brain, or a subset of regions in the brain. As one non-limiting example, metabolite topographies can be generated using a truncated atlas that only contains the limbic regions of the brain. In other instances, metabolite topographies can be generated for other organs, such as the heart. In these implementations, an appropriate anatomical atlas (e.g., a heart atlas) can be used to associate regions of the heart, such as the territories perfused by each of the major coronary arteries, with the metabolite data.

In another implementation, the metabolite topography generated for an organ such as the brain can be used as a comparison to gauge the metabolite signal from another region, which may or may not be in the anatomical atlas used to generate the topography. For example, the hyperpolarized $^{13}$C-lactate signal produced within an intracranial tumor can be converted to a tumor lactate z-score by: (1) computing the patient's brain lactate topography, (2) computing the mean and the standard deviation of the topography, (3) subtracting the topography mean from the tumor lactate signal, and (4) then dividing by the standard deviation of the topography. This tumor lactate z-score can then be compared with the tumor lactate z-score from previous patients that have and haven't responded to treatment, in order to predict the treatment response for the patient. Similarly, the metabolite topography from a subject can be compared to other subjects, or to metabolite topographies acquired from the same subject, but from a different time (e.g., comparing a post-treatment metabolite topography with a pre-treatment metabolite topography to assess the efficacy of that treatment).

Figure 1:
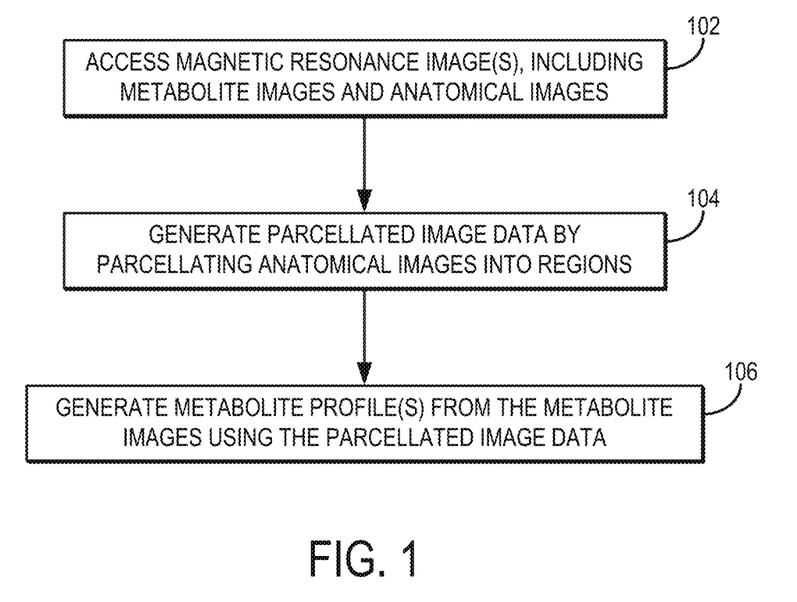
FIG. 1 is a flowchart setting forth the steps of an example method for generating metabolite profiles that indicate metabolite topography.

Referring now to FIG. 1, a flowchart is illustrated as setting forth the steps of an example method for generating metabolite profiles from magnetic resonance images and for monitoring, tracking, or otherwise comparing changes in those profiles over time or relative to normative data.

The method includes accessing magnetic resonance images with a computer system, as indicated at step 102. For instance, two sets of magnetic resonance images can be accessed: one indicative of magnetic resonance signals measured from a metabolite (i.e., metabolite images) and one depicting anatomical structures (i.e., anatomical images). The metabolite images are indicative of magnetic resonance signals measured from a metabolite, and in some embodiments these metabolite images can include images from the same slice that each correspond to different metabolites. For example, the magnetic resonance images can be indicative of a $^{13}$C-labelled metabolite, such as [1-$^{13}$C]lactate, [1-$^{13}$C]bicarbonate, and/or [1-$^{13}$C]pyruvate. In some other instances, the metabolite images can be indicative of an non-hypepolarized (e.g., endogenous) metabolite. The anatomical images can be a set of T1-weighted images acquired from the same subject from whom the metabolite images were obtained. For instance, the anatomical images can be T1-weighted images covering the whole brain of the subject. In some other instances, the anatomical images can depict other anatomical locations, such as the heart or other organs or organ systems.

The magnetic resonance images are accessed by retrieving previously acquired images from a memory or other suitable data storage or media. In some instances, accessing the magnetic resonance images may include retrieving acquired magnetic resonance data (e.g., k-space data) and reconstructing the images from those data. Additionally or alternatively, the magnetic resonance images can be accessed by the computer system by acquiring images with an MRI scanner and communicating the images to the computer system, which may be a part of the MRI system. Preferably, the magnetic resonance images represent 3D image volumes, such as 3D image volumes having contiguous slice coverage. Where the magnetic resonance images depict a subject's brain, the 3D image volume can provide whole brain coverage via this contiguous slice coverage.

Parcellated image data are generated by parcellating the anatomical images into regions, as indicated at step 104. For example, the images can be parcellated into different anatomical regions, such as different brain regions. As one example, the different brain regions may include a subset of regions in the brain, such as limbic regions. The different anatomical regions can also include regions or subregions within other organs or organ systems, such as different regions in the heart. This parcellation can be implemented in part using an anatomical atlas, such as an LPBA40 atlas or other suitable anatomical atlas. As an example, the output of this parcellation process can be a set of numerical labels (e.g., in a computer file or other data structure) that can be used to query the coordinates of all of the pixels in the anatomical images that correspond to each region in the atlas.

Metabolite profiles are generated from the metabolite images using the parcellated image data, as indicated at step 106. For example, the parcellation labels contained in the parcellated image data can be used to query or otherwise retrieve coordinates for the pixels in the metabolite images for each region, and the mean value for these pixels can be computed. The mean pixel values computed from the metabolite images for each region can be referred to as a metabolite profile for the subject. A normalized version of this metabolite profile can be generated, for example, by converting the sequence of mean metabolite pixel values from each region to a z-score.

As another example, parcellation labels contained in the parcellated image data can be used to query or otherwise retrieve coordinates for the pixels in the metabolite images for each region and ratios of metabolite signals within and/or across different regions can be computed and used as the metabolite profile(s). For instance, the ratio between different metabolites in the same region can be computed and used as a metabolite profile. As one non-limiting example, the ratio of lactate-to-pyruvate can be computed.

These metabolite profiles can be generated for a particular subject and then compared to normative data, such as a population-averaged normal metabolite profile, in order to detect disease, progression of disease, response to therapy, and so on. The metabolite profiles could be used, for instance, to enable early detection or monitoring of neurodegenerative diseases, such as Alzheimer's disease and Parkinson's disease. For example, the lactate z-score topography for a patient suspected of suffering from early Alzheimer's disease could be compared with the metabolite topographies of normal subjects of similar age. Regions with lactate z-scores outside the normal range of variability between subjects could indicate early metabolic changes associated with disease. The metabolite profiles could also be used to measure the response to therapy in such neurodegenerative diseases, as the aforementioned lactate z-scores outside the normal range of variability between subjects could return closer to the normal z-score for that region in response to the therapy, if that therapy was having the desired restorative effect on the metabolic state of the brain. The metabolite profiles could still also be used in connection with other neurological conditions, including psychiatric disorders such as bipolar disorder.

In an example study, metabolite profiles were generated from magnetic resonance data acquired from fourteen subjects. In this study, a 20-gauge intravenous catheter was inserted into the forearm of each subject before they were positioned supine and head-first in a 3.0T MRI scanner. A custom $^{13}$C head coil was used to acquire 3D dual-echo echo-planar imaging (DE-EPI) data of [1-$^{13}$C]lactate, [1-$^{13}$C]bicarbonate, and [1-$^{13}$C]pyruvate (axial, FOV 24×24×36 cm$^3$, 1.5 cm-isotropic resolution, 5 s temporal resolution, total of 60 s acquisition). At each timepoint, lactate, bicarbonate, and pyruvate images were acquired with net tip angles of 80 degrees, 80 degrees, and 11 degrees, respectively, which was spread across 24 excitations. After the metabolic images were obtained, the $^{13}$C head coil was replaced with a standard 8-channel $^1$H neurovascular array and standard anatomical images were acquired.

Each subject was injected with a 0.1 mmol/kg dose of [1-$^{13}$C]pyruvate prepared within a sterile fluid path. Each dose contained 1.47 grams of [1-$^{13}$C]pyruvic acid (Sigma Aldrich, St. Louise, Mo.) and AH111501 [Tris(8-carboxy-2,2,6,6 (tetra(methoxyethyl) benzo-[1,2-4,5]bis-(1,3)dithiole-4-yl)methyl sodium salt] (Syncom, Groningen, The Netherlands) in a 49:1 weight by weight ratio, respectively. This mixture was then hyperpolarized in a polarizer (General Electric SPINLab system, equipped with a quality control module) for three hours to achieve maximum polarization. Just prior to $^{13}$C image acquisition, the sample was dissolved within the sterile fluid pathway by 38 mL of heated and pressurized sterile water, transferred to the receiver vessel and mixed with 17.5 mL of a neutralizing solution (600 mmol/L NaOH, 333 mmol/L Tris base, and 333 mg/L disodium EDTA) plus 19 mL of sterile water. An aliquot of the final product was used for quality control assessment and the remainder (45 mL) was transferred into a Medrad (Medrad, Indianola Pa.) syringe for injection. The sample was injected at 4 mL/s followed by a 25 mL normal saline flush at 5 mL/s using a Spectris Solaris power injector.

The $^{13}$C image acquisition was initiated at the end of the saline flush. Volumetric images of [1-$^{13}$C]lactate, $^{13}$C-bicarbonate, and [1-$^{13}$C]pyruvate were acquired using a 3 T MRI scanner and a $^{13}$C head coil. Metabolite images covering a 3D volume (128×16×24 voxels/1.5 cm isotropic resolution) were acquired at 5 s intervals over the 60 s acquisition window.

The center frequency of the spectrally-selective echo-planar pulse sequence was toggled between the resonance frequencies of [1-$^{13}$C]lactate, $^{13}$C-bicarbonate and [1-$^{13}$C] pyruvate, resulting in separate volumetric images for each of these metabolites, every 5 s. Following the metabolite images, a standard suite of anatomical brain images was acquired with a conventional head coil, as noted above.

Figure 2:
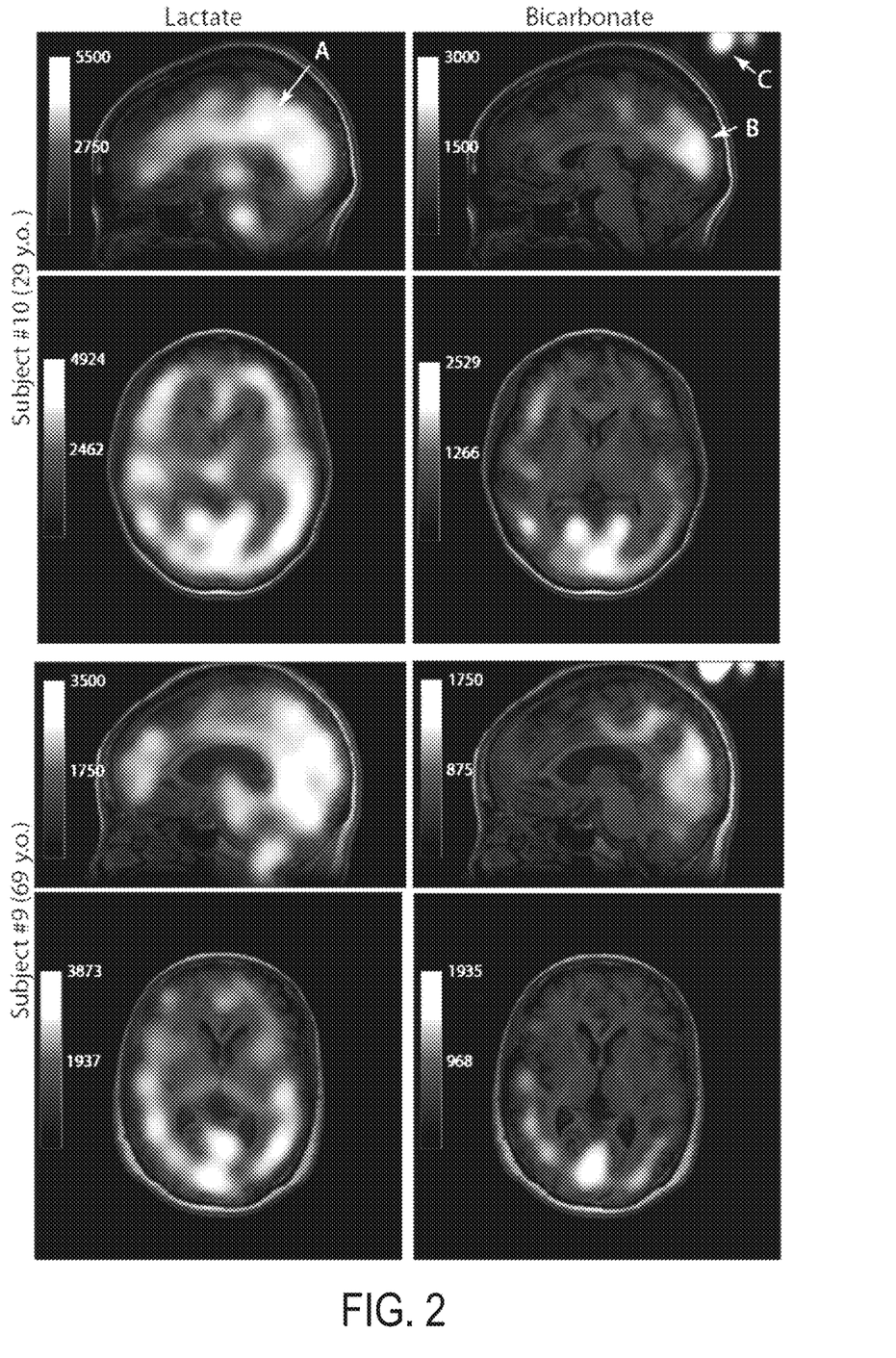
FIG. 2 shows representative images of $^{13}$C-lactate (left) and $^{13}$C-bicarbonate (right) from healthy female volunteers aged 29 (upper) and 69 (lower). The metabolite signals are displayed as color overlays on the corresponding T1-weighted anatomical images in grayscale, and were computed by summing the 12 timepoints over the 60 s acquisition window. The arrows indicate (A) the left precunius, (B) the left cunius and (C) the reference sample used for pre-scan calibration.

Representative metabolite images from two subjects are shown in FIG. 2. Lactate signal, which results from the conversion of [1-$^{13}$C]pyruvate to [1-$^{13}$C]lactate, was observed in all subjects with a consistent topography. Higher lactate signal was observed in cortical grey matter compared to white matter and was highest in the precuneus, cuneus and lingual gyrus. Bicarbonate signal, which indicates the flux of [1-$^{13}$C]pyruvate through the pyruvate-dehydrogenase complex on the mitochondrial membrane, resulting in $^{13}$C-bicarbonate, had a similarly consistent spatial distribution, and was also highest in many of the same regions as lactate, such as the occipital lobe.

To investigate how the observed spatial distribution of metabolite signals related to brain structure, the LONI pipeline processing environment was used to parcellate the metabolite images from each subject into the 56 regions contained in the LPBA40 atlas. The mean metabolite signal was computed for each region from each subject, for both lactate and bicarbonate. These values were normalized by converting to a z-score (the number of standard deviations from the mean of all regions within a single subject). This normalization accounts for any global scaling of the data for an individual subject, such the signal-enhancement level of the injected $^{13}$C-pyruvate and any difference in substrate delivery to the brain.

Figure 3:
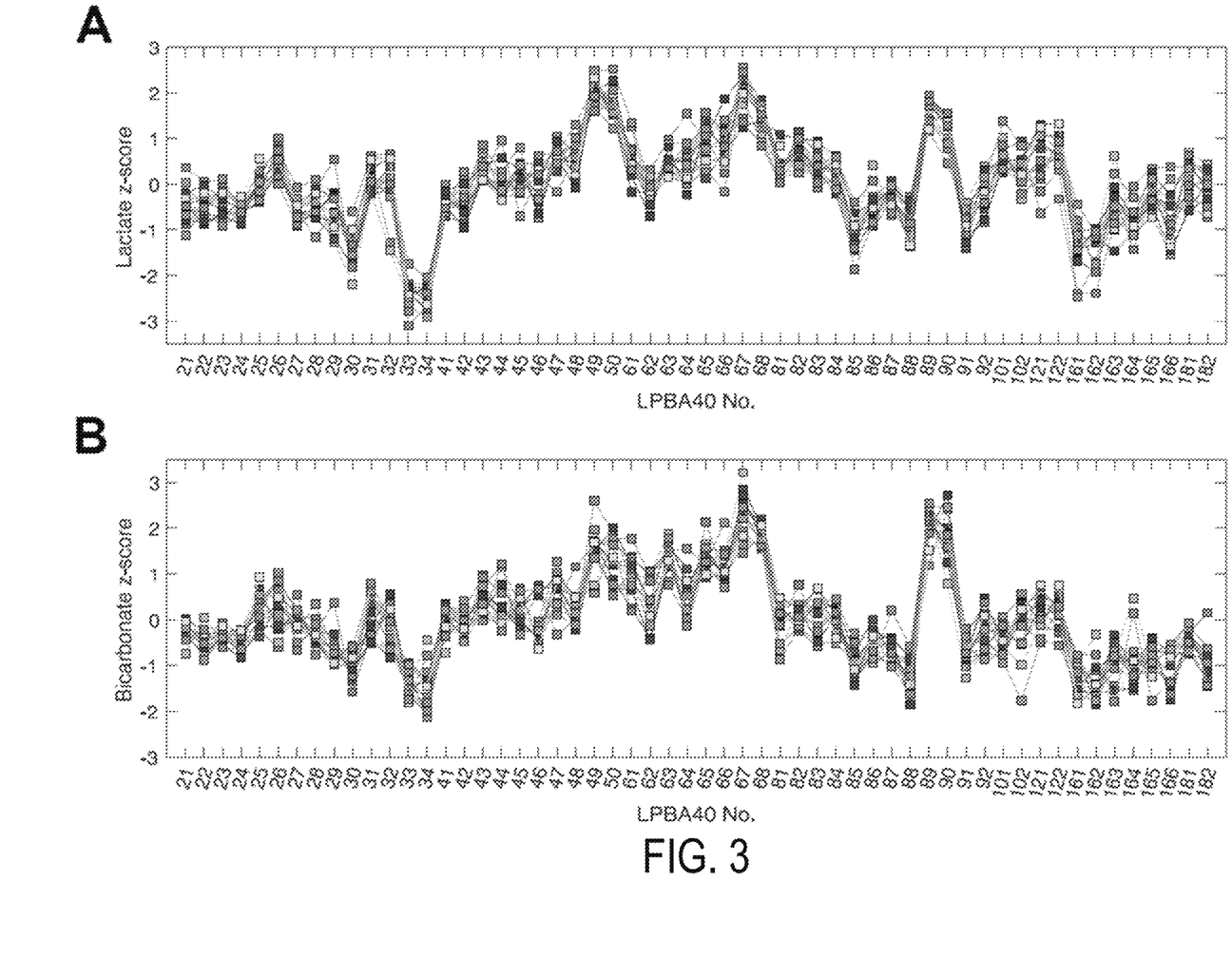
FIG. 3 shows metabolite profiles indicating the topography of normalized lactate and bicarbonate signals across subjects (N=14). (A) Lactate and (B) bicarboante z-scores plotted vs. the LPBA40 atlas region labels, with each color showing a different subject.
Figure 4:
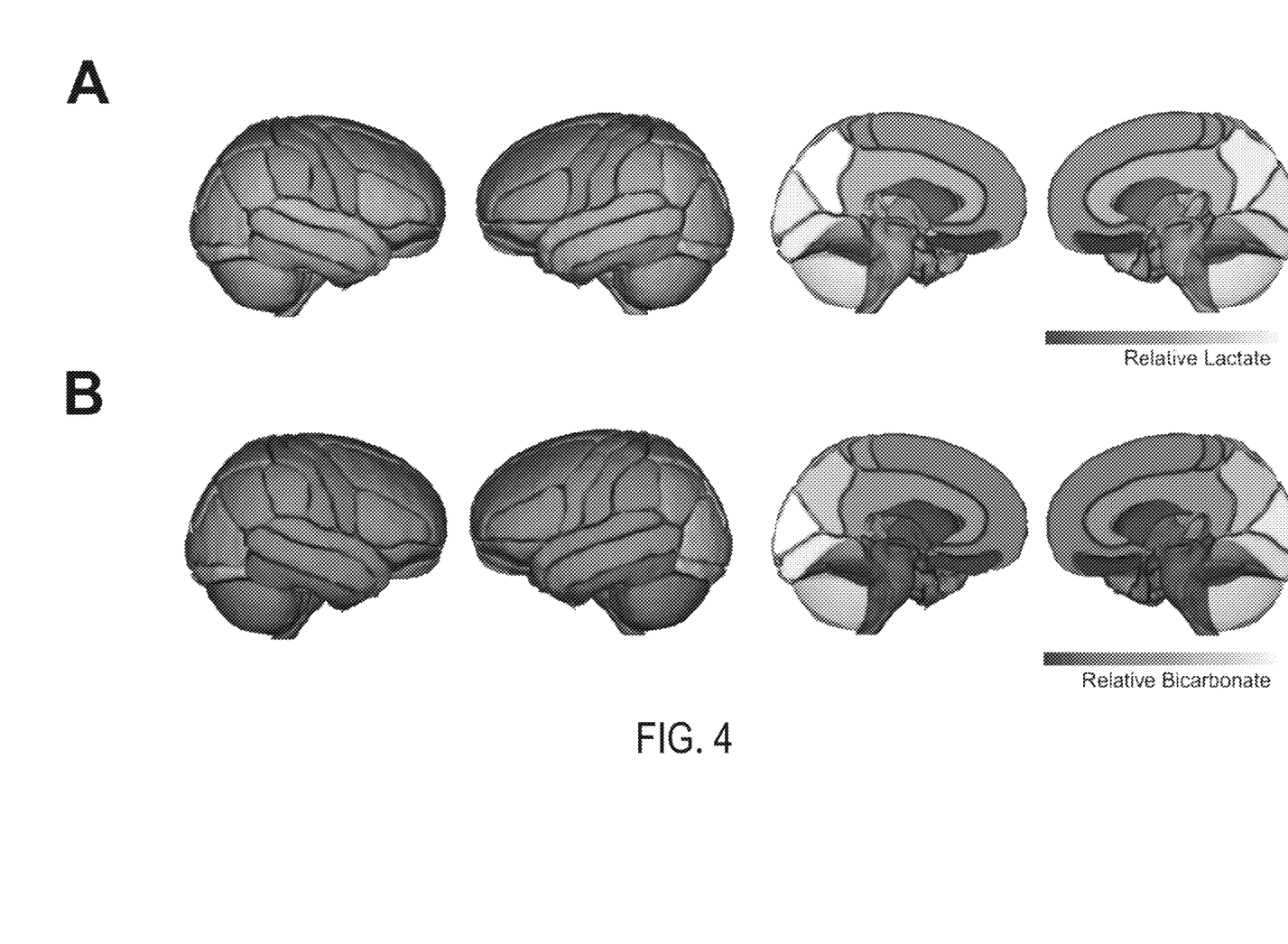
FIG. 4 shows consensus maps of the (A) lactate and (B) bicarbonate signals calculated from the mean z-score for each LPBA40 atlas region.

This analysis revealed a highly consistent spatial pattern of lactate signal across subjects, as seen in FIG. 3(*a*). One-way analysis of variance (ANOVA) was run to test for significant differences in lactate z-score among atlas regions, giving F=87.6 and p<10$^{-10}$. The concordance of the regional lactate signals between subjects was assessed by computing Kendall's coefficient of concordance (W) for the 56 regional z-scores for all subjects, giving W=0.83 and p<10$^{-4}$. The same analysis showed that the bicarbonate topography was similarly consistent between subjects (see FIG. 3(*b*)), with the W=0.82 and p<10$^{-4}$. Consensus lactate and bicarbonate maps were constructed from the mean z-score for each atlas region (see FIG. 4).

Figure 5:
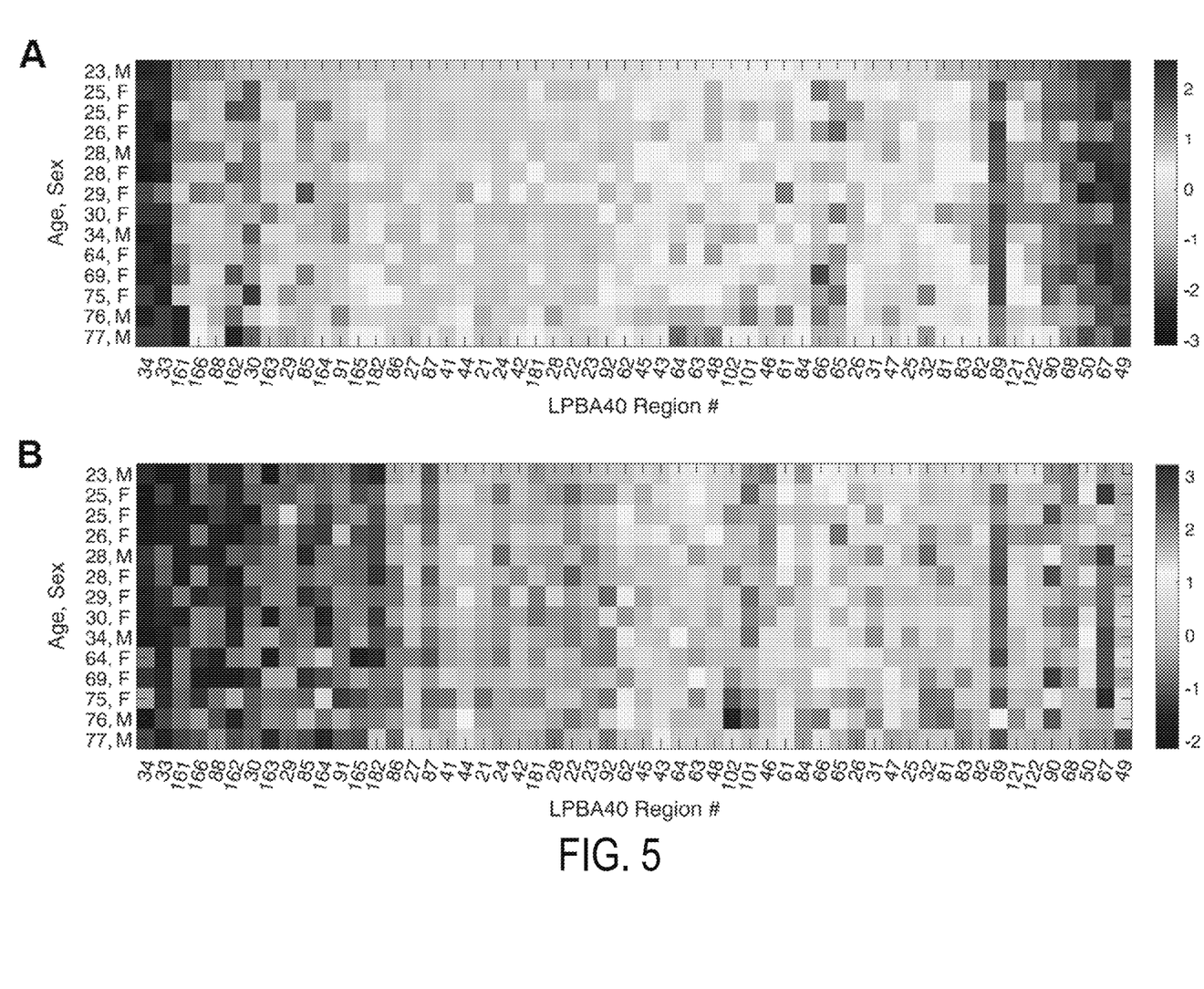
FIG. 5 shows heatmaps representing the lactate and bicarbonate z-scores with the regions in ascending order for lactate from one of the subjects (23,M). LPBA40 numbers and names of the regions with the 8 highest lactate z-scores are: (49) left precuneus, (67) left cuneus, (50) right precuneus, (68) right cuneus, (90) right lingual gyrus, (122) right cingulate gyrus, (121) left cingulate gyrus, (89) left lingual gyrus.

The consistency in the lactate topography suggests that the observed lactate signal differences across brain regions are a reflection of differing natural states of lactate homeostasis between these regions. It is notable that subjects at a wide range of ages were included in this study (see vertical axes in FIG. 5), so the observed lactate pattern appears to be largely age-independent.

Reduced OGI indicates regions where there is a net non-oxidative use of glucose, whereas hyperpolarized MRI shows all lactate created from the injected substrate, including lactate that ultimately ends up being used in oxidative phosphorylation. It should also be noted that the appearance of [1-$^{13}$C]lactate signal is dependent on a different set of glycolysis-related factors in comparison to the uptake of radiolabeled glucose and oxygen. These major factors are the expression levels of monocarboxylate transporters to transport pyruvate and lactate across lipid bilayers, the availability of the enzyme lactate dehydrogenase, and the local concentration of NADH, which is oxidized to NAD+ when pyruvate is reduced to lactate in the cytosol. Depletion of NADH has been shown to be the dominant factor in the $^{13}$C-lactate signal reduction observed after treating cancer cells, so regional variation in NADH concentration is a possible explanation for the observed lactate pattern.

Figure 6:
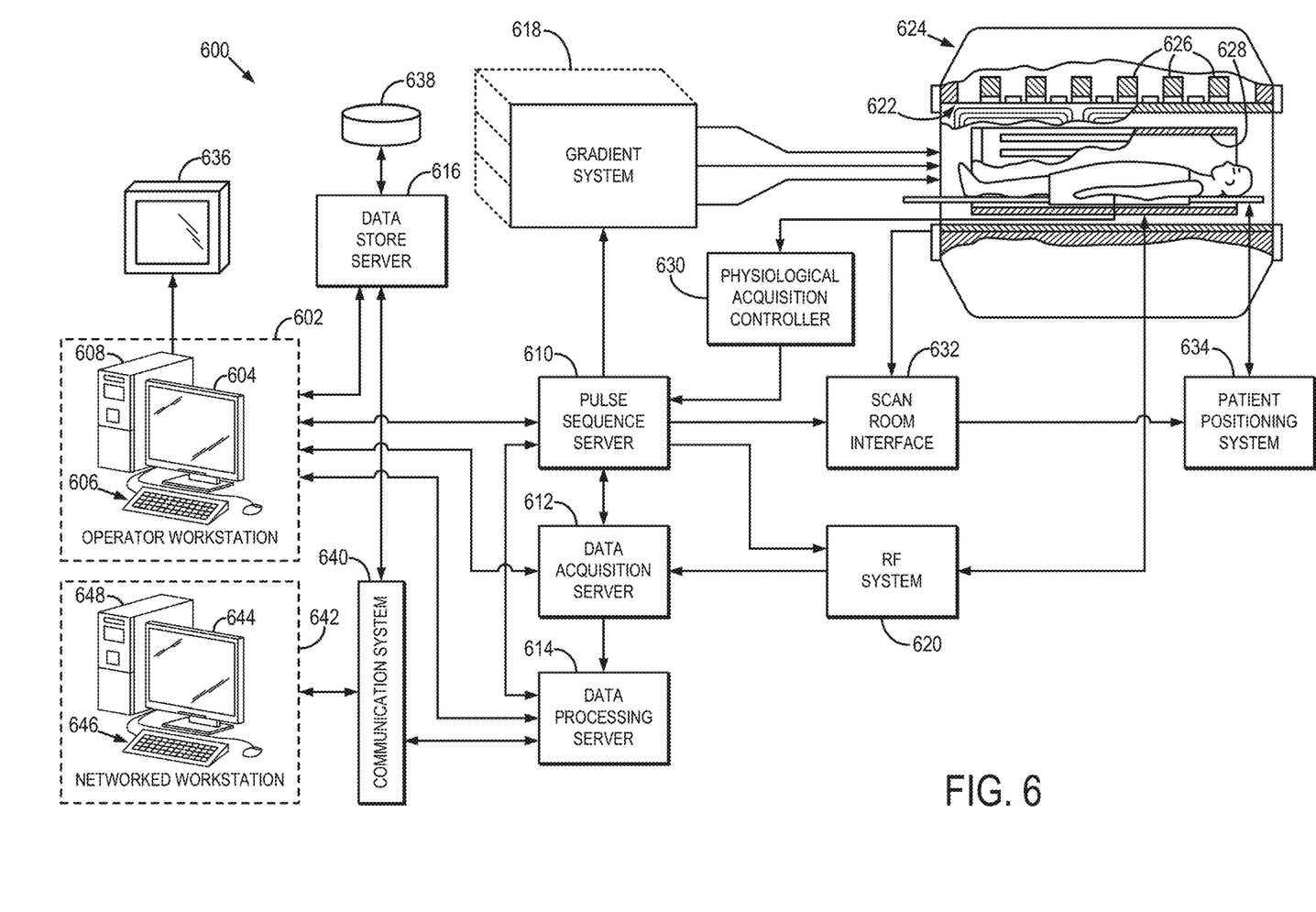
FIG. 6 is a block diagram of an example MRI system that can implement the methods described in the present disclosure.

Referring particularly now to FIG. 6, an example of an MRI system 600 that can implement the methods described here is illustrated. The MRI system 600 includes an operator workstation 602 that may include a display 604, one or more input devices 606 (e.g., a keyboard, a mouse), and a processor 608. The processor 608 may include a commercially available programmable machine running a commercially available operating system. The operator workstation 602 provides an operator interface that facilitates entering scan parameters into the MRI system 600. The operator workstation 602 may be coupled to different servers, including, for example, a pulse sequence server 610, a data acquisition server 612, a data processing server 614, and a data store server 616. The operator workstation 602 and the servers 610, 612, 614, and 616 may be connected via a communication system 640, which may include wired or wireless network connections.

The pulse sequence server 610 functions in response to instructions provided by the operator workstation 602 to operate a gradient system 618 and a radiofrequency ("RF") system 620. Gradient waveforms for performing a prescribed scan are produced and applied to the gradient system 618, which then excites gradient coils in an assembly 622 to produce the magnetic field gradients $G_x$, $G_y$, and $G_z$ that are used for spatially encoding magnetic resonance signals. The gradient coil assembly 622 forms part of a magnet assembly 624 that includes a polarizing magnet 626 and a whole-body RF coil 628.

RF waveforms are applied by the RF system 620 to the RF coil 628, or a separate local coil to perform the prescribed magnetic resonance pulse sequence. Responsive magnetic resonance signals detected by the RF coil 628, or a separate local coil, are received by the RF system 620. The responsive magnetic resonance signals may be amplified, demodulated, filtered, and digitized under direction of commands produced by the pulse sequence server 610. The RF system 620 includes an RF transmitter for producing a wide variety of RF pulses used in MRI pulse sequences. The RF transmitter is responsive to the prescribed scan and direction from the pulse sequence server 610 to produce RF pulses of the desired frequency, phase, and pulse amplitude waveform. The generated RF pulses may be applied to the whole-body RF coil 628 or to one or more local coils or coil arrays.

The RF system 620 also includes one or more RF receiver channels. An RF receiver channel includes an RF preamplifier that amplifies the magnetic resonance signal received by the coil 628 to which it is connected, and a detector that detects and digitizes the I and Q quadrature components of the received magnetic resonance signal. The magnitude of the received magnetic resonance signal may, therefore, be determined at a sampled point by the square root of the sum of the squares of the I and Q components:

$$M=\sqrt{I^2+Q^2} \qquad (1);$$

and the phase of the received magnetic resonance signal may also be determined according to the following relationship:

$$\varphi = \tan^{-1}\left(\frac{Q}{I}\right). \qquad (2)$$

The pulse sequence server 610 may receive patient data from a physiological acquisition controller 630. By way of example, the physiological acquisition controller 630 may receive signals from a number of different sensors connected to the patient, including electrocardiograph ("ECG") signals from electrodes, or respiratory signals from a respiratory bellows or other respiratory monitoring devices. These signals may be used by the pulse sequence server 610 to synchronize, or "gate," the performance of the scan with the subject's heart beat or respiration.

The pulse sequence server 610 may also connect to a scan room interface circuit 632 that receives signals from various sensors associated with the condition of the patient and the magnet system. Through the scan room interface circuit 632, a patient positioning system 634 can receive commands to move the patient to desired positions during the scan.

The digitized magnetic resonance signal samples produced by the RF system 620 are received by the data acquisition server 612. The data acquisition server 612 operates in response to instructions downloaded from the operator workstation 602 to receive the real-time magnetic resonance data and provide buffer storage, so that data is not lost by data overrun. In some scans, the data acquisition server 612 passes the acquired magnetic resonance data to the data processor server 614. In scans that require information derived from acquired magnetic resonance data to control the further performance of the scan, the data acquisition server 612 may be programmed to produce such information and convey it to the pulse sequence server 610. For example, during pre-scans, magnetic resonance data may be acquired and used to calibrate the pulse sequence performed by the pulse sequence server 610. As another example, navigator signals may be acquired and used to adjust the operating parameters of the RF system 620 or the gradient system 618, or to control the view order in which k-space is sampled. In still another example, the data acquisition server 612 may also process magnetic resonance signals used to detect the arrival of a contrast agent in a magnetic resonance angiography ("MRA") scan. For example, the data acquisition server 612 may acquire magnetic resonance data and processes it in real-time to produce information that is used to control the scan.

The data processing server 614 receives magnetic resonance data from the data acquisition server 612 and processes the magnetic resonance data in accordance with instructions provided by the operator workstation 602. Such processing may include, for example, reconstructing two-dimensional or three-dimensional images by performing a Fourier transformation of raw k-space data, performing other image reconstruction algorithms (e.g., iterative or backprojection reconstruction algorithms), applying filters to raw k-space data or to reconstructed images, generating functional magnetic resonance images, or calculating motion or flow images.

Images reconstructed by the data processing server 614 are conveyed back to the operator workstation 602 for storage. Real-time images may be stored in a data base memory cache, from which they may be output to operator display 602 or a display 636. Batch mode images or selected real time images may be stored in a host database on disc storage 638. When such images have been reconstructed and transferred to storage, the data processing server 614 may notify the data store server 616 on the operator workstation 602. The operator workstation 602 may be used by an operator to archive the images, produce films, or send the images via a network to other facilities.

The MRI system 600 may also include one or more networked workstations 642. For example, a networked workstation 642 may include a display 644, one or more input devices 646 (e.g., a keyboard, a mouse), and a processor 648. The networked workstation 642 may be located within the same facility as the operator workstation 602, or in a different facility, such as a different healthcare institution or clinic.

The networked workstation 642 may gain remote access to the data processing server 614 or data store server 616 via the communication system 640. Accordingly, multiple networked workstations 642 may have access to the data processing server 614 and the data store server 616. In this manner, magnetic resonance data, reconstructed images, or other data may be exchanged between the data processing server 614 or the data store server 616 and the networked workstations 642, such that the data or images may be remotely processed by a networked workstation 642.

Figure 7:
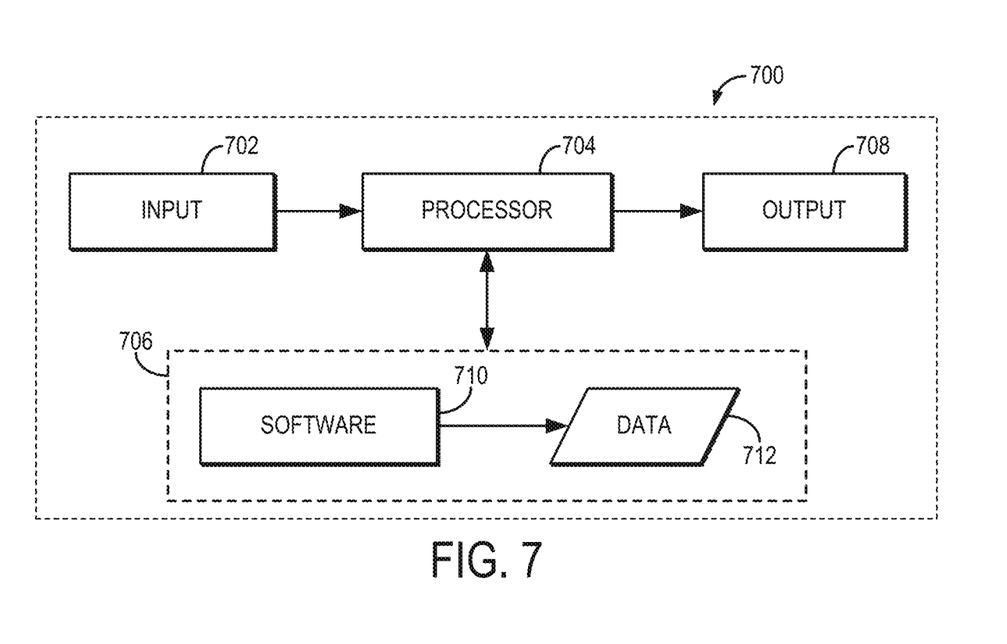
FIG. 7 is a block diagram of an example computer system that can implement the methods described in the present disclosure.

Referring now to FIG. 7, a block diagram of an example of a computer system 700 that can perform the methods described in the present disclosure is shown. The computer system 700 generally includes an input 702, at least one hardware processor 704, a memory 706, and an output 708. Thus, the computer system 700 is generally implemented with a hardware processor 704 and a memory 706.

In some embodiments, the computer system 700 can be a workstation, a notebook computer, a tablet device, a mobile device, a multimedia device, a network server, a mainframe, one or more controllers, one or more microcontrollers, or any other general-purpose or application-specific computing device.

The computer system 700 may operate autonomously or semi-autonomously, or may read executable software instructions from the memory 706 or a computer-readable medium (e.g., a hard drive, a CD-ROM, flash memory), or may receive instructions via the input 702 from a user, or any another source logically connected to a computer or device, such as another networked computer or server. Thus, in some embodiments, the computer system 700 can also include any suitable device for reading computer-readable storage media.

In general, the computer system 700 is programmed or otherwise configured to implement the methods and algorithms described in the present disclosure. For instance, the computer system 700 can be programmed to generate metabolite profiles from magnetic resonance images, as described.

The input 702 may take any suitable shape or form, as desired, for operation of the computer system 700, including the ability for selecting, entering, or otherwise specifying parameters consistent with performing tasks, processing data, or operating the computer system 700. In some aspects, the input 702 may be configured to receive data, such as data acquired with an MRI system. Such data may be processed as described above to generate metabolite profiles and to monitor, track, or otherwise compare changes in those profiles over time or relative to normative data. In addition, the input 702 may also be configured to receive any other data or information considered useful for implementing the methods described above.

Among the processing tasks for operating the computer system 700, the one or more hardware processors 704 may also be configured to carry out any number of post-processing steps on data received by way of the input 702.

The memory 706 may contain software 710 and data 712, such as data acquired with an MRI system, and may be configured for storage and retrieval of processed information, instructions, and data to be processed by the one or more hardware processors 704. In some aspects, the software 710 may contain instructions directed to generating metabolite profiles from magnetic resonance images and to monitoring, tracking, or otherwise comparing changes in those profiles over time or relative to normative data.

In addition, the output 708 may take any shape or form, as desired, and may be configured for displaying magnetic resonance images (e.g., anatomical images, metabolite images), metabolite profiles, consensus maps, and heatmaps, in addition to other desired information.

In some embodiments, any suitable computer readable media can be used for storing instructions for performing the functions and/or processes described herein. For example, in some embodiments, computer readable media can be transitory or non-transitory. For example, non-transitory computer readable media can include media such as magnetic media (e.g., hard disks, floppy disks), optical media (e.g., compact discs, digital video discs, Blu-ray discs), semiconductor media (e.g., random access memory ("RAM"), flash memory, electrically programmable read only memory ("EPROM"), electrically erasable programmable read only memory ("EEPROM")), any suitable media that is not fleeting or devoid of any semblance of permanence during transmission, and/or any suitable tangible media. As another example, transitory computer readable media can include signals on networks, in wires, conductors, optical fibers, circuits, or any suitable media that is fleeting and devoid of any semblance of permanence during transmission, and/or any suitable intangible media.

The present disclosure has described one or more preferred embodiments, and it should be appreciated that many equivalents, alternatives, variations, and modifications, aside from those expressly stated, are possible and within the scope of the invention.

The invention claimed is:

1. A method for producing a metabolite profile from magnetic resonance images, the method comprising:

(a) accessing with a computer system, magnetic resonance images acquired from a subject, wherein the magnetic resonance images comprise:
  a plurality of metabolite images having pixel values indicative of magnetic resonance signals associated with a metabolite;
  a plurality of anatomical images that depict anatomical structures in the subject;
(b) generating parcellated image data by parcellating the anatomical images into a plurality of parcellated regions, wherein each pixel of the parcellated image data is associated with a region from an anatomical atlas;
(c) generating a metabolite profile for the subject from the plurality of metabolite images and using the parcellated image data, wherein the metabolite profile is generated by:
  (i) selecting a given region from the plurality of parcellated regions;
  (ii) retrieving pixel values from the plurality of metabolite images using the coordinates for the given region in the parcellated image data;
  (iii) computing a mean pixel value for the given region by computing a mean of the retrieved pixel values; and
  (iv) repeating steps (i) though (iii) for each of a number of the plurality of parcellated regions in order to generate a sequence of mean pixel values, wherein the metabolite profile comprises the sequence of mean pixel values.

2. The method as recited in claim 1, wherein the metabolite images comprise a plurality of sets of metabolite images, each set of metabolite images having pixel values indicative of magnetic resonance signals associated with a different metabolite, and wherein step (c) includes generating a different metabolite profile for each of the plurality of metabolites.

3. The method as recited in claim 1, wherein the magnetic resonance images are acquired using a hyperpolarized $^{13}$C imaging technique.

4. The method as recited in claim 1, wherein the magnetic resonance images comprise three-dimensional images.

5. The method as recited in claim 4, wherein the three-dimensional images comprise a series of contiguous slices.

6. The method as recited in claim 1, wherein step (c) includes converting the metabolite profile to a normalized metabolite profile by converting the mean pixel values in the sequence of mean pixel values to a z-score.

7. The method as recited in claim 1, wherein the metabolite is an endogenous metabolite.

8. The method as recited in claim 7, wherein the endogenous metabolite comprises at least one of lactate or glutamate.

9. The method as recited in claim 1, wherein the anatomical atlas comprises a brain atlas.

10. The method as recited in claim 9, wherein the plurality of parcellated regions correspond to limbic regions of the subject's brain.

11. The method as recited in claim 1, wherein the anatomical atlas comprises a heart atlas.

12. A method for producing a metabolite profile from magnetic resonance images, the method comprising:
(a) accessing with a computer system, magnetic resonance images acquired from a subject, wherein the magnetic resonance images comprise:
  a plurality of metabolite images, each of the metabolite images having pixel values indicative of magnetic resonance signals associated with a metabolite;
  a plurality of anatomical images that depict anatomical structures in the subject;
(b) generating parcellated image data by parcellating the anatomical images into a plurality of parcellated regions, wherein each pixel in the parcellated image data is associated with a region from an anatomical atlas;
(c) generating a metabolite profile for the subject from the plurality of metabolite images and using the parcellated image data, wherein the metabolite profile is generated by:
  (i) selecting a first region from the plurality of parcellated regions;
  (ii) retrieving first pixel values from the plurality of metabolite images using the coordinates for the first region in the parcellated image data;
  (iii) selecting a second region from the plurality of parcellated regions;
  (iv) retrieving second pixel values from the plurality of metabolite images using the coordinates for the second region in the parcellated image data;
  (v) computing a ratio value between the first pixel values and the second pixel values; and
  (vi) repeating steps (i) though (v) for each of a number of first and second regions in the plurality of parcellated regions in order to generate a sequence of ratio values, wherein the metabolite profile comprises the sequence of ratio values.

13. The method as recited in claim 12, wherein the first region and the second region are a same parcellated region and the first pixel values correspond to a first metabolite and the second pixel values correspond to a second metabolite that is different from the first metabolite.

14. The method as recited in claim 12, wherein the first region is different from the second region.

15. The method as recited in claim 12, wherein the magnetic resonance images are acquired using a hyperpolarized $^{13}$C imaging technique.

16. The method as recited in claim 12, wherein the metabolite is an endogenous metabolite.

17. The method as recited in claim 12, wherein the anatomical atlas comprises a brain atlas.

18. The method as recited in claim 17, wherein the plurality of parcellated regions correspond to limbic regions of the subject's brain.

19. The method as recited in claim 12, wherein the anatomical atlas comprises a heart atlas.

* * * * *